United States Patent
Howell et al.

(10) Patent No.: US 6,533,782 B2
(45) Date of Patent: Mar. 18, 2003

(54) MEDICAL DEVICE WITH IMPROVED WIRE GUIDE ACCESS

(75) Inventors: Douglas A. Howell, Cape Elizabeth, ME (US); Matthew P. Carter, Dobson, NC (US); William S. Gibbons, Jr., Winston-Salem, NC (US); Jason D. Foushee, Winston-Salem, NC (US)

(73) Assignee: Wilson-Cook Medical Incorporated, Winston-Salem, NC (US)

( * ) Notice: Subject to any disclaimer, the term of this patent is extended or adjusted under 35 U.S.C. 154(b) by 35 days.

(21) Appl. No.: 09/851,810

(22) Filed: May 9, 2001

(65) Prior Publication Data

US 2002/0049423 A1 Apr. 25, 2002

Related U.S. Application Data

(60) Provisional application No. 60/205,192, filed on May 18, 2000.

(51) Int. Cl.[7] ............................................. A61M 5/178
(52) U.S. Cl. ..................... 606/47; 604/164.13; 604/528
(58) Field of Search ................... 606/47, 46; 604/528, 604/164.13

(56) References Cited

U.S. PATENT DOCUMENTS

| | | |
|---|---|---|
| 4,033,331 A | 7/1977 | Guss et al. |
| 4,641,654 A | 2/1987 | Samson et al. |
| 4,838,269 A | 6/1989 | Robinson et al. |
| 5,061,273 A | 10/1991 | Yock |
| 5,358,509 A | 10/1994 | Fine et al. |
| 5,366,464 A | 11/1994 | Belknap |
| 5,397,302 A | 3/1995 | Weaver et al. |
| 5,398,687 A | 3/1995 | Abell |
| 5,536,248 A | 7/1996 | Weaver et al. |
| 5,599,299 A | 2/1997 | Weaver et al. |
| 5,599,300 A | 2/1997 | Weaver et al. |
| 5,599,324 A | 2/1997 | McAlister et al. |
| 5,628,761 A | 5/1997 | Rizik |
| 5,697,948 A | 12/1997 | Marin et al. |
| 5,766,191 A | 6/1998 | Trerotola |
| 5,788,681 A | 8/1998 | Weaver et al. |
| 5,800,444 A | 9/1998 | Ridinger et al. |
| 5,843,028 A | 12/1998 | Weaver et al. |
| 5,843,091 A | 12/1998 | Holsinger et al. |
| 5,868,698 A | 2/1999 | Rowland et al. |
| 5,921,971 A | 7/1999 | Agro et al. |
| 6,007,522 A | 12/1999 | Agro et al. |
| 6,017,340 A | 1/2000 | Cassidy et al. |
| 6,106,487 A * | 8/2000 | Duane et al. ............... 600/585 |
| 6,129,697 A * | 10/2000 | Drasler et al. ............... 604/22 |
| 6,152,910 A | 11/2000 | Agro et al. |
| 6,176,843 B1 | 1/2001 | DiCaprio et al. |
| 6,228,052 B1 | 5/2001 | Pohndorf |
| 6,248,092 B1 | 6/2001 | Miraki et al. |
| 2002/0052638 A1 * | 5/2002 | Zadno-Azizi ............... 623/1.2 |

FOREIGN PATENT DOCUMENTS

| | | | |
|---|---|---|---|
| DE | 4330400 | * | 5/1995 |
| FR | 2647005 | | 11/1990 |
| WO | 9744082 | | 11/1997 |

* cited by examiner

*Primary Examiner*—John A. Jeffery
(74) *Attorney, Agent, or Firm*—Charles W. Agnew

(57) ABSTRACT

A medical apparatus assembly (10) comprises a medical device (11) that includes a side port assembly 13 adapted to combine a first pathway (37) for infusion of fluids with a second pathway (38) for wire guide (12) into a first passageway (26) while the second passageway (27) includes the third pathway (39), which comprises a control member (24), such as an electrical wire. The side port assembly is configured such that the first passageway communicates with both a first port (16), such as a fitting for connecting to a syringe, and a second port (15) which includes a sealing mechanism (32), such as a Tuohy-Borst fitting, thereby allowing the wire guide to be preloaded, instead of requiring it to be removed prior to infusing fluids. Optionally, a third port (43) may be included when external communication with the second passageway, is desired, such as balloons or baskets.

14 Claims, 3 Drawing Sheets

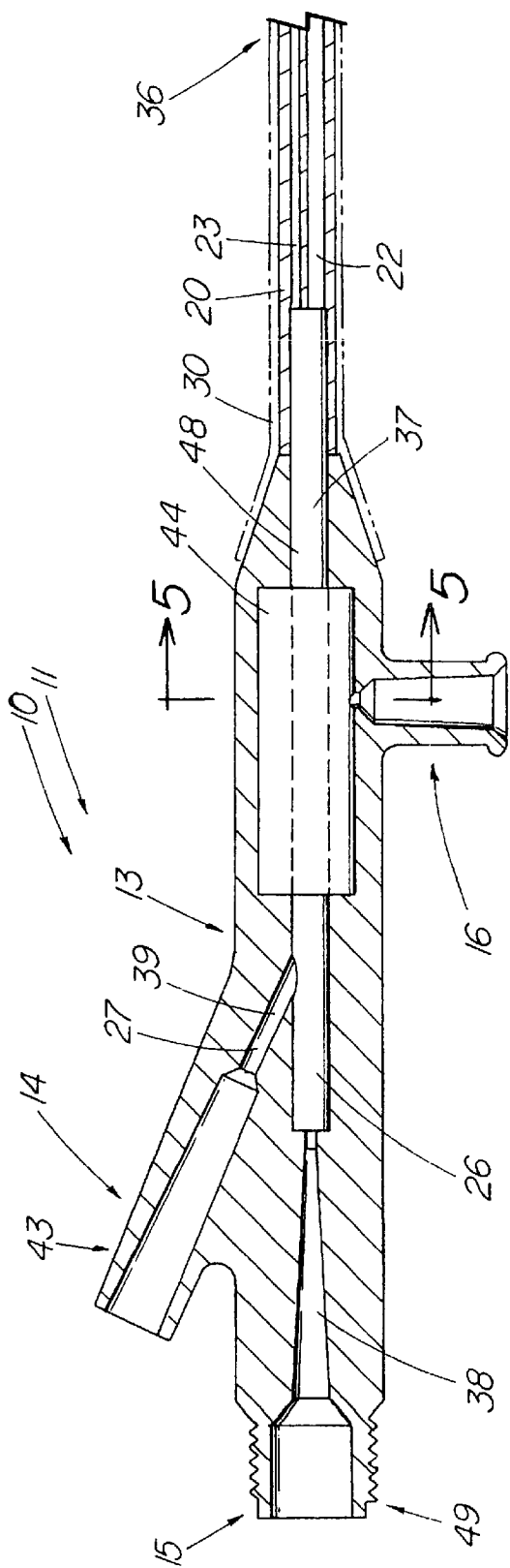
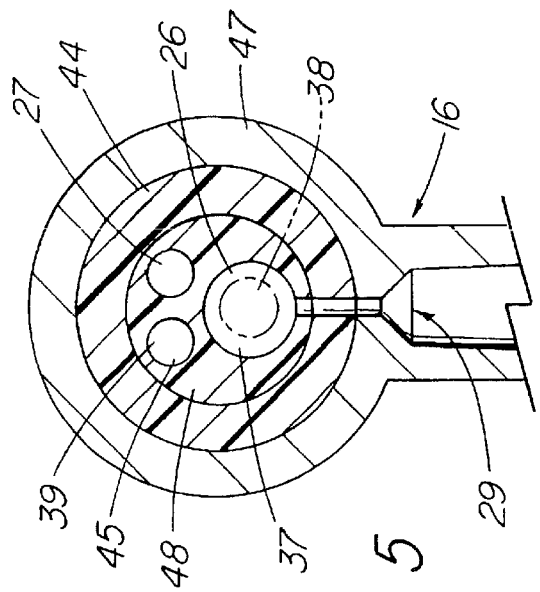
FIG. 4
FIG. 5

MEDICAL DEVICE WITH IMPROVED WIRE GUIDE ACCESS

CROSS-REFERENCE TO RELATED APPLICATIONS

This application claims priority of provisional application Ser. No. 60/205,192, filed May 18, 2000.

TECHNICAL FIELD

This invention relates to medical devices, more particularly to catheters used in surgical procedures.

BACKGROUND OF THE INVENTION

Sphincterotomes are used in the biliary system as part of an Endoscopic Retrograde Cholangiopancreatography (ERCP) procedure when the Sphincter of Oddi becomes constricted due to disease or trauma. The sphincterotome, which is typically introduced through the working channel of an endoscope, serves both to cannulate the ductal system and enlarge the opening by delivery of electrical current to a cutting wire. Most standard sphincterotome models, e.g., the MINI-TOME PC™ (Wilson Cook Medical, Inc., Winston-Salem, N.C.), include a wire guide side port connected distal to the handle into which a wire guide is introduced once access is obtained to the biliary system. The wire guide provides continual access across the sphincter as well as a means to exchange other devices that may be used. The wire guide port usually contains a luer fitting for injection of contrast media or other liquid materials. Unfortunately, this must be done with the wire guide removed so that the syringe or delivery apparatus can be coupled to the side port. Adding a separate fitting on the side port for the wire guide would create a portal for leakage of material, especially when contrast is being injected therethrough. To maintain separate injection and wire guide lumens, in addition to the required lumen for the electrical conductor wire, either results in either smaller lumens than would be optimal or necessary, or requires that the sphincterotome catheter be made larger, also something that is not desirable, especially for a device used within an endoscope. The same problem can be found in other devices, such as balloon catheters, and retrieval devices, such as baskets. Accommodating the control member of the apparatus, the wire guide, and still provide for the injection of contrast media, requires three separate pathways. Unfortunately, providing for all three to be simultaneously operable within a device is often unacceptable due to size constraints. What is needed is a medical device, such as a sphincterotome, that utilizes a control member, that can allow the wire guide to be used while the fluids (e.g., contrast media, saline) are being injected, without requiring a third lumen such that the device will pass through a standard endoscope.

SUMMARY OF THE INVENTION

The foregoing problems are also solved and a technical advance is achieved with a medical device, such as the illustrative sphincterotome, having a side port assembly which includes a first port, such as a standard luer lock fitting, which is adapted for injection of fluids or infusate (a first pathway), and a second port, such as a Tuohy-Borst fitting, that is configured for introduction of a standard medical wire guide (a second pathway) where the fitting on the second port can be made to seal around the wire guide to prevent the passage of air or fluids, while still permitting longitudinal movement of the wire guide. The first and second ports communicate with a first lumen of the catheter portion, such as via a shared first passageway (e.g., a cannula), while a second passageway lumen of the catheter portion contains the controlling element apparatus (e.g., electrical conductor (sphincterotome wire), actuating mechanism, inflation lumen(s), etc.) of the device (the third pathway), which may extend to the proximal handle of the device via a second passageway. Combining the fluid pathway and the wire guide pathway into a single passageway within the apparatus, permits the second pathway to be dedicated to housing the control apparatus. Otherwise, a third large lumen would have been required to accomodate all three pathways, thereby increasing the diameter of the catheter. By making the wire guide pathway (second port) sealable, such as with a Tuohy-Borst fitting, contrast media, saline, water, or other liquid media can be injected around the wire guide. For example, in the illustrative sphincterotome, the present invention allows a wire guide to be preloaded into the sphincterotome prior to the cannulation and cutting procedure, advantageously making the entire procedure easier and quicker to perform. In addition, having the preloaded wire guide extending from the distal tip, increases the physician's ability to cannulate closed sphincters and other strictures due to the smaller diameter of the wire guide. The same concept can be extended to other types of devices used with wire guides, such as balloons, catheters, baskets, snares, deflectable devices, etc., wherein the controlling element is disposed in the second passageway, while the wire guide and injected fluid share the first passageway.

BRIEF DESCRIPTION OF THE DRAWINGS

FIG. 3 depicts a cross-sectional view taken along line 3—3 of FIG. 1;

FIG. 4 depicts a partially sectioned side view of a second embodiment of the present invention; and FIG. 5 depicts a cross-sectional view taken along line 5—5 of FIG. 4.

DETAILED DESCRIPTION

Figure 1:
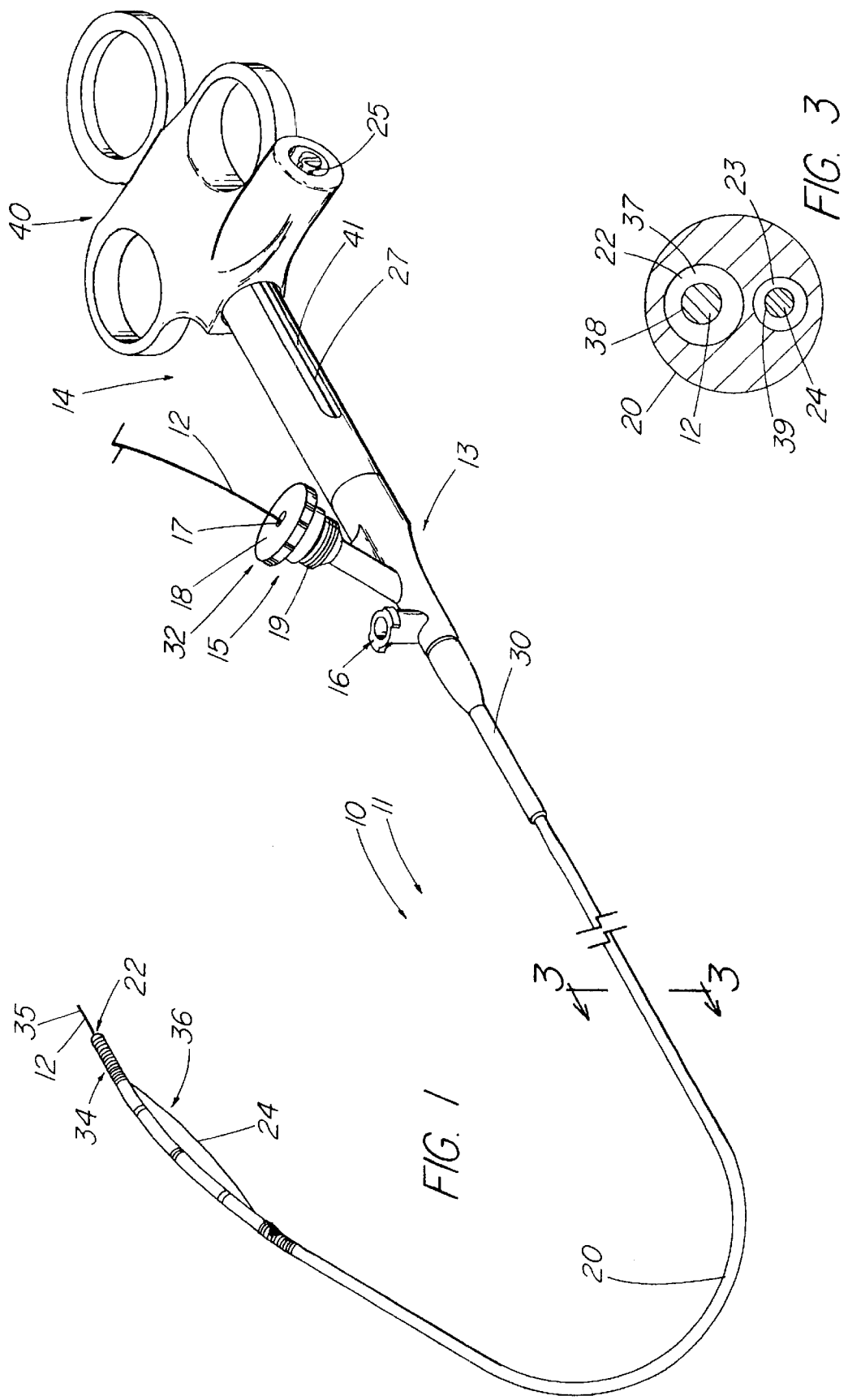
FIG. 1 depicts a pictorial view of the illustrative embodiment of the present invention.
Figure 2:
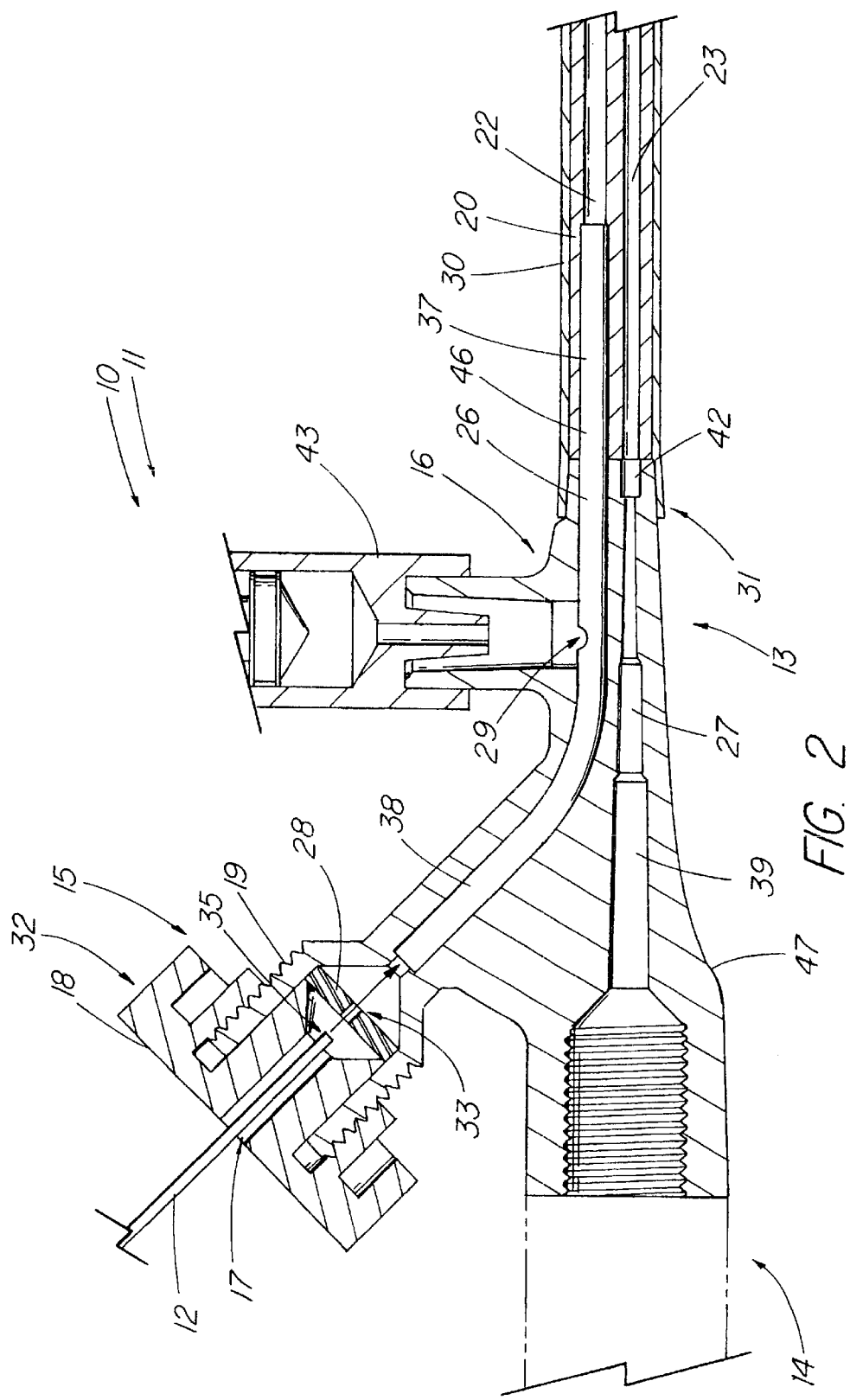
FIG. 2 depicts a partially sectioned side view of the port of the embodiment of FIG. 1.

FIGS. 1–2 depicts a medical apparatus 10 of the present invention, such as a sphincterotome assembly, comprising a medical device 11, such as an electrosurgical device or sphincterotome, comprising a handle assembly 14, an elongate portion 20, which in the illustrative embodiment is a 6 Fr sphincterotome catheter (tapered distally to 4.5 Fr tip), and a working member 36, which comprises a cutting wire in the in the illustrative embodiment, situated about the distal portion 34 of the catheter portion 20. The handle assembly 14 is used herein to generally refer to the proximal portion of the device from which the operator manipulates the device 11 and through which all ancillary devices and materials are introduced. The handle assembly 14 includes a side port assembly 13 that further comprises a first port 16, such as a standard luer lock fitting for the infusion of fluids or infusate, and a sealable, second port 15, such as a standard Tuohy-Borst fitting, that can be used for the introduction of a wire guide 12 which is typically used during a sphincterotomy procedure, such as to cannulate a stricture at the Sphincter of Oddi. In the illustrative embodiment, the side port assembly 13 is conveniently located distal the grasping portion 40 of the handle assembly 14. As depicted in FIG. 2, the first and second ports 15,16 function as the proximal access points to the first pathway 37 for fluid infusion and the second pathway 38 for the wire guide, respectively. Both pathways 37,38 feed into a shared first passageway 26, such as the illustrative tubular conduit or cannula 46, (typically thin-wall stainless steel) that in turn, communicates with a first lumen 22 which generally extends throughout the catheter portion 20 of the device 11. The cannula 46 comprising the first passageway 26 serves to guide and protect the wire guide 12 as it traverses the first passageway 26 and feeds into the first lumen 22, as well as providing a conduit to carry the fluid comprising the first pathway 37 as the two pathways 37,38 converge within the first passageway 26. The second lumen 23 of the catheter portion 20 serves to accommodate a third pathway 39, which comprises a control member 24 that extends distally to operate or activate the working member 36 of the device 10. In illustrative sphincterotome 11 of FIG. 1, the control member 24 comprises the electrical conductor or wire 24 that extends to the distal portion 34 of the device 11, where it becomes the cutting wire 36 used to burn or slice through tissue forming a stricture and enlarger the opening. In the illustrative embodiment, the second passageway 27 includes an optional cannula 41 that houses and protects the sphincterotome wire 24 within the side port assembly 13 of the handle portion 14. Proximally, the sphincterotome wire 24 connects inside the handle assembly 14 to a standard electrical connector 25 located on the side of the handle assembly. Distally, the first and second passageways 26,27 connect with the proximal end 31 of the sphincterotome catheter portion 20, thereby communicating with the first and second lumens 22,23, respectively. To provide further protection to the wire 24, the distal portion 42 of the second passageway 27 is enlarged at the junction with the second lumen 23 of the sphincterotome catheter. The cannula 46 comprising the first passageway 26 extends into the first lumen 22, providing a means of attachment and reinforcement at the junction of the passageways 26,22. As shown in FIG. 1, an outer sleeve 30 is typically placed over this junction to provide added reinforcement and support. It should be noted that the illustrative sphincterotome is merely exemplary and one skilled in the medical arts should be able to conceive of design variations that still would fall within the scope of the invention.

FIG. 3 depicts a cross-sectional view of catheter portion 20 of the sphincterotome 11, containing a first and a second lumen 22,23 as shown in FIG. 3. Typically, the first lumen 22 is somewhat larger that the second lumen 23 for the purpose of accommodating a wire guide 12, while having sufficient space to permit the delivery of fluids, such as contrast media or saline, therearound. In the illustrative sphincterotome, the second lumen 23 diameter is generally about 0.023". In order to accommodate a standard 0.025" wire guide 12 (actual diameter 0.020" to 0.025"), the first lumen 22 would preferably have a diameter of about 0.040" to 0.044", with a more preferred diameter of 0.041" to 0.042". Generally, this diameter still permits a viscous fluid, such as most contrast media, to be infused though the remaining space of the lumen 22 with the wire guide 12 in place. These dimensions are merely exemplary, and can be appropriately scaled upward or downward, depending on the size of the wire guide 12 used, and the diameter of the working channel of the endoscope. The cross-sectional shape of a particular lumen 22,23 is not especially critical for an understanding of the invention and may be round, "D" or crescent-shaped, or some other configuration. While it generally most desirable to limit the number of lumens to keep the O.D. of the device 10 as small as possible, particularly if it is to be used within an endoscope having a channel size of 2.8 mm, additional lumens may also be included, if desired such that the pathways 37,38,39 of the device are distributed in some other manner or combination. Restricting the number of lumens to two is preferred, however, as long as the design allows for continual presence of a wire guide during infusion of fluids, such that the wire guide 12 need not be removed and can be pre-loaded, if desired.

In the illustrative embodiment of FIG. 1, a standard wire guide 12 (e.g., a standard biliary 0.025" PTFE-coated nitinol wire guide) is shown preloaded into the sphincterotome 11 via the first port 16. Depicted in FIG. 2, the port 16 includes a sealing mechanism 32 comprising a seal 28, such as an o-ring, and a tightening component 18, such as a threaded cap. The tightening component 18 is threaded on to the threaded receiving portion 19 of the first port 15. As the tightening component 18 is turned clockwise, the aperture 33 in the seal 28 become narrower, with the seal 28 eventually being urged tightly against the wire guide 12, substantially or completely preventing passage of fluid therearound. The pressure of the seal 28 is such that it still permits longitudinal movement of the wire guide 12 without first requiring the cap 18 to be loosened. To preload the wire guide 12 into the sphincterotome 11, it is fed through the external opening 17 in the second port 15, through the aperture 33 of the seal 28, and into the first passageway 26 (cannula 46). From there, the wire guide 12 is advanced through the first lumen 22 until it nears the distal tip 21 of the sphincterotome. Optionally, a section of wire (not shown) or other protective means, such as metal or plastic tubing, is placed in the most distal portion 34 of the lumen 22, or over the outside of the distal portion 34, to maintain the desired shape of the distal portion 34 that includes the cutting wire 36 until it is time to deploy the device within a patient. At that time, the wire is removed and the distal end 35 of the wire guide is advanced beyond the distal tip 21 of the sphincterotome 11 to assist with cannulation of the sphincter.

In the illustrative embodiment of FIGS. 1–2, the first port 16 includes a standard luer fitting for receiving a fluid delivery device 43, such as a syringe. The first port 16 communicates with the first passageway 26 and first lumen 22 via an opening 29 along the first passageway 26, depicted in FIG. 2 as an aperture formed in cannula 46, although alternative configurations as possible, such as side branches extending from cannula 46 or first passageway 26 that communicate with the first port 16. The fluids are infused through the first passageway 26 and first lumen 22, which also accommodates the wire guide 12, where they exit at the distal end 21 of the spincterotome. As shown in FIG. 1, the pathway 39 that comprises the electrode wire terminates proximal the distal end 21 with the exposed wire 24 functioning as the cutting portion 36 of the sphincterotome.

FIGS. 4–5 depicts a second embodiment of the present invention in which the second port 16 through which the wire guide 12 is introduced is located at the proximal end 47 of the apparatus, from where it feeds into a multilumen conduit 48 which houses the first and second passageways 26,27, which include the three pathways 37,38,39. The first and second passageways 26,27 of the conduit 48 feed into the first lumen 26 and the second and third lumens 45, respectively. The first passageway 26 of the illustrative embodiment, housing the first and second pathways 37,38, comprises a sufficient diameter, e.g. 0.040" to 0.042", to accommodate a standard 0.025" wire guide 112, while having sufficient additional space to infuse a liquid therearound. In contrast to FIG. 1 where the third pathway 39 includes a conductor wire 24, the second passageway 27 in the embodiment of FIGS. 4–5 comprises a conduit that feeds a pair of 0.015" inflation lumens 45 (FIG. 5) that extend through the catheter portion and communicate with an inflatable member 36 (not shown) such as a balloon or bag. The number and size of the lumens 45 can be variable, depending on the application. The illustrative side arm assembly 13 is also adaptable for other devices in which the control member 24 resides within the second member and functions as an actuating member for a retrieval device, such as a basket or snare. Typically, the actuating member of a basket or other retrieval device is much larger than the conductor wire of the sphincterotome, often requiring a larger second lumen 23, e.g., 0.40" to 0.048". In the illustrative embodiment of FIGS. 4–5, the multilumen conduit 48 includes an optional manifold slug 44 which is useful in the process of molding the side arm adapter housing 47 around the multilumen conduit 48. A opening or scive 29 is formed in the multilumen conduit 48 and manifold slug 44 to gain external access to the first passageway 26 as shown in FIG. 5. The opening 29 communicates with the first port 16, which is a luer lock for connecting to a syringe (not shown) for flushing or injecting media in the illustrative embodiment. The second port 15, which typically includes a standard Tuohy-Borst fitting (not shown), is positioned at the proximal end 49 of the handle assembly 14 in this particular embodiment. A third port 43 is included on the side arm adapter 13 that communicates with the third pathway 39 comprising the control member 24, which extends through the second passageway 27 and second lumen 23 to operate the work piece 36. In one embodiment wherein the work piece 36 comprises an inflatable member (not shown), the third port 43 is configured for connection to a stopcock (not shown) or other apparatus for inflating the inflatable member. In other embodiments, the third pathway 39 can accommodate an actuating member 24, such as a cable, for manipulating a retrieval device 36, such as basket or snare, a deflectable member, or another well-known medical device. In the latter group of devices, the third port 43 may be eliminated if the actuating member 24 is connected to part of the handle assembly 14 for operation of the work piece 36, which would be similar to the embodiment of FIGS. 1–4.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

What is claimed is:

1. A medical apparatus to be used in combination with a medical wire guide, comprising:
    a handle assembly that includes a side port assembly comprising at least a first port and a second port;
    a catheter portion attached to the handle assembly, the catheter portion including at least a first and a second lumen extending at least partially therethrough;
    a first pathway adapted for the delivery of a fluid therethrough, the first pathway communicating with the first port;
    a second pathway adapted for accommodating the medical wire guide, the second pathway communicating with the second port;
    a third pathway extending distally from the handle assembly through the second lumen, the third pathway adapted to permit remote operation of a working member located about the distal end of the catheter portion; and
    wherein the second port includes a sealing mechanism adapted to seal around the wire guide when placed therein, and substantially preventing the loss of fluid from the second port, and wherein the first and second pathways each extend through the first lumen, such that the wire guide can be placed and remain within the second pathway while the fluid comprising the first pathway is infused therethrough.

2. The medical device of claim 1, wherein the medical device comprises an electrosurgical device with the third pathway comprising a control member that includes an electrical conductor communicating with a working member.

3. The medical device of claim 2, wherein the electrosurgical device comprises a sphincterotome with the working member comprising a cutting wire.

4. The medical device of claim 1 further including the wire guide, the wire guide being preloaded within the second pathway of the medical device.

5. The medical device of claim 1 wherein the second pathway includes a tubular conduit communicating with both the second port and the first lumen, the conduit including an opening that communicates with the first port.

6. The medical device of claim 1, wherein the medical device comprises a balloon catheter with the third pathway adapted to deliver an infusate via one or more inflation lumens.

7. The medical device of claim 1, wherein the medical device comprises a retrieval device with the control member comprising an actuating member.

8. A sphincterotome used in combination with a medical wire guide, comprising:
    a handle assembly that includes a side port assembly comprising at least a first port and a second port, the side port assembly further including a first passageway and a second passageway;
    a catheter portion attached to the handle assembly, the catheter portion including at least a first and a second lumen extending at least partially therethrough;
    a first pathway adapted for the delivery of an infusate therethrough, the first pathway communicating with the first port;
    a second pathway adapted for accommodating the medical wire guide, the second pathway communicating with the second port, the second port including a sealing mechanism that is sealable about the wire guide;
    a third pathway comprising an electrical conductor that is disposed within the second passageway; and
    wherein the first and second pathways each feed into the first passageway and extend through the first lumen, such that the wire guide can remain within the second pathway while the infusate is infused through the first pathway.

9. The sphincterotome of claim 8, wherein the first port and the second port each feed a first passageway, the first passageway comprising an elongate cannula.

10. The sphincterotome of claim 9, wherein the second port is located proximal the first port, the second port communicating with the cannula via one end thereof, and with the first port communicating with the cannula via an aperture located therealong.

11. A medical device used in combination with a wire guide, comprising:
- a handle assembly that includes a side port assembly comprising at least a first port, a second port, and a third port;
- a catheter portion attached to the handle assembly, the catheter portion including at least a first and a second lumen extending at least partially therethrough;
- a first pathway adapted for the delivery of a fluid therethrough, the first pathway communicating with the first port;
- a second pathway adapted for accommodating a wire guide, the second pathway communicating with the second port, the second port being sealable about the wire guide;
- a third pathway communicating with a third port and extending through the second passageway and second lumen, the third pathway adapted to permit remote operation of a working member located about the distal end of the catheter portion; and
- wherein the first and second pathways each extend through the first lumen, such that the wire guide can be placed and remain within the second pathway while the fluid is infused through the first pathway.

12. The medical apparatus of claim 11, wherein the third pathway comprises an actuating member and the working member comprises at least one of group consisting of a basket, snare, or deflectable device.

13. The medical apparatus of claim 11, wherein the third pathway comprises at least one inflation lumen and the working member comprises an inflatable member.

14. A sphincterotome used in combination with a medical wire guide, comprising:
- a handle assembly that includes a side port assembly comprising at least a first port and a second port, the side port assembly further including a first passageway and a second passageway;
- a catheter portion attached to the handle assembly, the catheter portion including at least a first and a second lumen extending at least partially therethrough;
- a first pathway adapted for the delivery of a fluid therethrough, the first pathway communicating with the first port;
- a second pathway comprising the medical wire guide, the second pathway communicating with the second port, the second port including a sealing mechanism that is sealable about the wire guide;
- a third pathway comprising an electrical conductor that is disposed within the second passageway; and
- wherein the first and second pathways each feed into the first passageway and extend through the first lumen, such that the wire guide can remain within the second pathway while the infusate is infused through the first pathway, and wherein the first passageway comprises a cannula that extends at least partway into the first lumen of the catheter portion.

* * * * *